United States Patent [19]
Baker

[11] Patent Number: 6,113,598
[45] Date of Patent: Sep. 5, 2000

[54] RADIOFREQUENCY MEDICAL INSTRUMENT AND METHODS FOR VESSEL WELDING

[76] Inventor: James A. Baker, 4292-P Wilkie Way, Palo Alto, Calif. 94306

[21] Appl. No.: 09/251,850

[22] Filed: Feb. 17, 1999

Related U.S. Application Data

[60] Provisional application No. 60/074,808, Feb. 17, 1998, provisional application No. 60/075,275, Feb. 19, 1998, and provisional application No. 60/076,164, Feb. 26, 1998.

[51] Int. Cl.[7] ........................................ A61B 18/14
[52] U.S. Cl. ........................ 606/51; 606/38; 606/40; 606/52
[58] Field of Search ................ 606/45, 46, 48–52, 606/38, 40

[56] References Cited

U.S. PATENT DOCUMENTS

| | | | |
|---|---|---|---|
| 5,151,102 | 9/1992 | Kamiyama et al. | 606/51 |
| 5,269,780 | 12/1993 | Roos | 606/51 |
| 5,290,387 | 3/1994 | Boebel et al. | 606/51 |
| 5,403,312 | 4/1995 | Yates | 606/50 |
| 5,443,463 | 8/1995 | Stern et al. | 606/51 |
| 5,693,051 | 12/1997 | Schulze et al. | 606/51 |
| 5,702,390 | 12/1997 | Austin et al. | 606/48 |
| 5,833,690 | 1/1998 | Yates et al. | 606/51 |
| 5,891,141 | 4/1999 | Rydell | 606/51 |
| 6,039,733 | 3/2000 | Buysse et al. | 606/40 |

*Primary Examiner*—Lee Cohen
*Attorney, Agent, or Firm*—Fish & Neave; Nicola A. Pisano

[57] ABSTRACT

Methods and apparatus are provided for welding or sealing vessels or organs by collapsing a vessel with a jaw-like structure, applying an RF current between first and second bi-polar electrodes, and directing path of the RF current using a channeling electrode disposed intermediate the first and second bi-polar electrodes. The jaw-structure may be configured to progressively collapse the section of tissue to may squeeze fluids out of the lumen of the vessel. In addition, or alternatively, the jaw-structure may be configured to elongated the collapsed section of vessel to alter its impedance characteristics prior to application of RF energy. The device also may include one or more sensors providing signals to a power controller that modulates application of RF energy to the vessel.

19 Claims, 11 Drawing Sheets

RADIOFREQUENCY MEDICAL INSTRUMENT AND METHODS FOR VESSEL WELDING

REFERENCE TO RELATED APPLICATIONS

This application claims priority from U.S. provisional patent application Ser. Nos. 60/074,808, filed Feb. 17, 1998, 60/075,275, filed Feb. 19, 1998, and 60/076,164, filed Feb. 26, 1998. This application also is related to co-pending U.S. patent application Ser. No. 08/920,291, filed Aug. 28, 1997, now U.S. Pat. No. 5,957,920, and Ser. No. 09/191,413, filed Nov. 12, 1998, which are hereby incorporated herein by reference.

FIELD OF THE INVENTION

This invention relates to methods and apparatus for utilizing RF energy to seal tubular vessels of organs, and more particularly for delivering RF energy in a controlled manner to denature proteins in the endothelial tissues to form a thermal biological weld to close the vessel or organ.

BACKGROUND OF THE INVENTION

In both open and endoscopic surgeries, it often is necessary to seal or weld blood vessels, both veins and arteries, ranging in size from less than 1 mm in diameter to more than 6 mm in diameter. For example, in subfacial endoscopic perforator surgery or SEPS, a series of perforator vessels in a patient's leg are sealed closed to alleviate venous ulcerations. In a typical SEPS procedure, the surgeon uses a mechanically deformable clip to pinch off such perforator vessels. A single clip may not seal a vessel in a reliable manner and the surgeon typically uses multiple clips on each perforator vessel to assure an effective seal. It would be preferable to seal a vessel without leaving a metal clip implanted in the patient's body.

Radiofrequency ("RF") instruments for sealing blood vessels have been developed. An example of a previously known bi-polar grasper, shown in FIG. 1A, typically applies from 40 watts to 100 watts or more of power to the exterior of a vessel to cauterize such vessels or vascularized tissue masses. To use such previously known bi-polar instruments, a blood vessel is squeezed between the opposing jaw faces of the grasper (see FIG. 1B). Each jaw face comprises a conductive electrode 2A, 2B. When operating in a bi-polar fashion, the RF current generally flows between electrodes 2A and 2B, and directly "across" vessel 3, as indicated by the arrow in FIG. 1B.

Additionally, there may be stray RF current flow in circuitous low resistance routes, e.g., outwardly along the vessel and then through surrounding tissue, to reach the other electrode, as indicated by arrow 4 in FIG. 1C. This type of stray RF current flow is undesirable. For example, in a SEPS procedure or when sealing a branch vein of any arterial conduit that may be mobilized for a bypass, it is undesirable to have stray RF current affect the arterial conduit.

In using a previously known device such as depicted in FIGS. 1A–1C, the impedance of the tissue of the vessel wall changes continuously during the application of RF, making sealing erratic. The high levels of power typically used in previously known devices (e.g., 40 to 100 watts), makes the tissue impedance levels undesirably change very rapidly. At power levels ranging from 40 to 100 watts, impedance levels typically will increase within a few seconds to a level such that RF energy flow is impeded or restricted altogether, and may contribute to an increase in stray RF current. Moreover, the vessel walls often will not be fused together over a sufficient area to provide an effective seal.

Furthermore, previously known devices, such as shown in FIGS. 1A–1C, which simply clamp the vessel walls together, often entrap blood between the luminal surfaces. This trapped blood acts as a heat sink and may adversely affect the uniformity of RF thermal effects. It has been observed that the entrapment of blood within the lumen significantly interferes with the binding characteristics of the denatured proteins that are created and that comprise the amalgam for fusing the vessel walls together.

It would therefor be desirable to provide an RF energy delivery system, and methods of use, that reduce the unwanted effects of variable tissue impedance, thereby allowing an effective energy delivery profile in the tissue targeted for welding.

It also would be desirable to provide an RF energy delivery system, and methods of use, wherein an openable/closeable jaw structure reduces the risk of entrapping blood between the vessel walls.

It further would be desirable to provide an RF energy delivery system, and methods of use, that reduce tissue charring and smoke, which can obscure the physician's view, particularly in endoscopic surgeries.

It still further would be desirable to provide an RF energy delivery system, and methods of use, that reduce the outward spread of thermal effects along a vessel (e.g., to protect a main vessel when sealing branch vessels close to main vessel).

It also would be desirable to provide an RF energy delivery system, and methods of use, that substantially reduce stray RF currents from traveling outwardly along a vessel away from the portion targeted for welding.

SUMMARY OF THE INVENTION

In view of the foregoing, it is an object of this invention to provide an RF energy delivery system, and methods of use, that reduce the unwanted effects of variable tissue impedance, thereby allowing an effective energy delivery profile in the tissue targeted for welding.

It is also an object of this invention to provide an RF energy delivery system, and methods of use, wherein an openable/closeable jaw structure reduces the risk of entrapping blood between the vessel walls.

It is a further object of the present invention to provide an RF energy delivery system, and methods of use, that reduce tissue charring and smoke, which can obscure the physician's view, particularly in endoscopic surgeries.

It is another object of this invention to provide an RF energy delivery system, and methods of use, that reduce the outward spread of thermal effects along a vessel.

It still further is an object of this invention to provide an RF energy delivery system, and methods of use, that substantially reduce stray RF currents from traveling outwardly along a vessel away from the portion targeted for welding.

These and other objects of the present invention are accomplished by providing apparatus and methods for applying RF energy to tissue that: (1) progressively engage a vessel or organ to minimize the amount of blood entrapped in the lumen, and thereafter maintains the vessel walls in close approximation under appropriate pressures for welding; (2) deliver bi-polar RF energy longitudinally along the length of the vessel to create an effective seal; (3) direct the path of the RF current along the vessel lumen; and optionally (4) stretch the targeted vessel segment prior to application of the RF energy to alter its impedance characteristics.

A preferred embodiment of an instrument of the present invention comprises an introducer member that carries a distal working end with an openable/closeable jaw structure for engaging a targeted vessel section. The jaw structure is moveable between an open position and a closed position by a suitable mechanism disposed in a handle portion coupled to the introducer member. The jaw structure has an upper jaw side or member and a lower jaw side or member with cooperating opposing jaw faces.

Each jaw face defines right-side and left-side portions that cooperate with portions of the opposing jaw face. The upper jaw side includes a central projecting portion. In a first family of embodiments, the lower jaw has deflectable right-side and left-side elements with a central receiving structure or gap for receiving the opposing side's projecting portion. In an alternative embodiment, the central projecting portion of the upper jaw side comprises one or more resiliently deformable elements that progressively flatten as the upper and lower jaw sides close together.

The cooperating jaw faces in both families of embodiments serve several purposes. First, the upper and lower jaw faces are arranged so that they progressively engage the vessel from the center of the targeted vessel section and cause blood within the lumen to be squeezed out of the targeted area. Second, the upper and lower jaw faces may be configured to stretch the vessel before RF delivery to alter the impedance characteristics of the targeted vessel section. Also, the arrangement of the upper and lower jaws faces allow the jaw structure to accommodate vessels of different diameters and maintain the luminal surfaces (when collapsed) within a particular pressure range that is suitable for an RF-induced thermal biological weld.

In accordance with the principles of the present invention, the jaw structure carries an electrode configuration that allows RF energy delivery at very low power levels (0.50 to 30.0 watts), yet creates thermal effects sufficient to weld luminal tissues. First and second bi-polar electrodes, disposed on right-side and left-side portions of the jaw assembly, provide a flow of current longitudinally through the targeted vessel section. Optionally, one or more non-active "channeling" electrodes, i.e., that are insulated from the first and second bi-polar electrodes and the RF power supply, may be positioned at least partially intermediate to the first and second bi-polar electrodes. One or more sensors also may be provided to measure temperatures or impedance levels of the section of the vessel targeted for welding, contemporaneous with RF energy delivery.

A preferred method of the present invention for welding closed the lumen of a blood vessel or organ comprises: (1) delivering an RF current along a vessel section between first and second spaced-apart bi-polar electrodes; and (2) directing the RF current between the first and second electrodes through a path in tissue generally proximate to an intermediate channeling electrode that is in longitudinal contact with the vessel section.

Optionally, prior to application of the RF current, the vessel may be progressively engaged by first engaging a center section and then pushing blood outwardly from the vessel lumen toward the first and second ends of the vessel section. Alternatively, or in addition, the impedance characteristics of the vessel section targeted for welding may be altered by stretching or extending the targeted vessel section to alter the extracellular fluid ("ECF") content level of the vessel wall and endothelium.

BRIEF DESCRIPTION OF THE DRAWINGS

Additional objects and advantages of the invention will be apparent from the following description, the accompanying drawings and the appended claims, in which:

DETAILED DESCRIPTION OF THE INVENTION

Figure 1A:
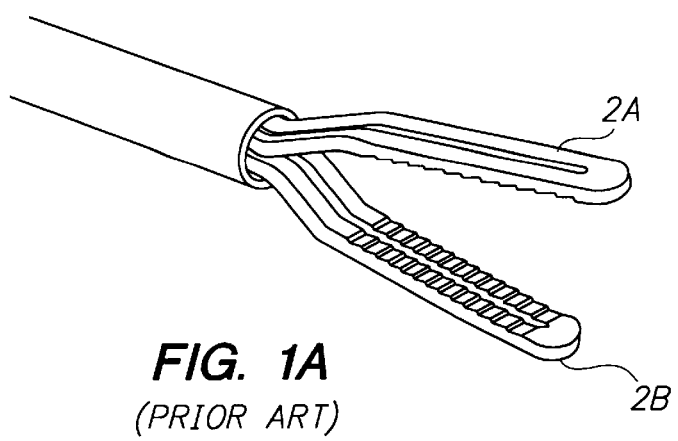
FIGS. 1A–1C are perspective views of a jaw structure of a previously known bi-polar radiofrequency device and its use in cautery.

The present invention provides apparatus and methods for controlling the effects of RF energy delivery to a blood vessel captured within a working end of an instrument to improve RF energy delivery profiles for welding small and large blood vessels (or other organs) quickly and efficiently.

The apparatus and methods of the present invention may be used to seal or weld blood vessels in a number of different procedures. For purposes of illustration, the present invention is described for use in performing subfacial endoscopic perforator surgery (SEPS). In this disclosure, the term vessel is defined to include any artery or vein of any size, and further includes tissue/vessel combinations or vascularized tissue masses where an individual vessel cannot be separated from the tissue. The apparatus and methods of the present invention also find application in sealing the lumens of other organs or anatomic structures having lumens with collagen-containing tissues capable of forming biological glue.

It is known that many beneficial results, such as the reduction of charring, smoke, and stray RF current, may be achieved by reducing RF power levels. In accordance with the principles of the present invention, RF power levels may be reduced to 0.50 watts to 30.0 watts, delivered, for example, over a period of 5 to 20 seconds (depending on vessel size) and still achieve the significant thermal effects required to weld tissue.

The mechanism of tissue welding is complex and is not completely understood. The application of RF energy to tissue results in heat which denatures tissue proteins in the vessel walls and in the endothelial lining of the vessel, which includes a high percentage of collagen. The heat denatures the proteins in the collagen-containing tissues into a proteinaceous amalgam, which forms a thermal biological glue in a temperature range from 65° C. to 90° C. The integrity of the sealing effect depends greatly on the conductive characteristics of the target tissue, which in turn effect denaturation of proteins.

To form an effective seal, it is necessary to maintain a desired temperature over the targeted vessel section for an appropriate time period to develop a uniform layer of denatured proteins. Even partial denaturation of the endothelial lining involves disruption of cellular membranes, thereby allowing cellular fluids and extracellular matrix materials to intermix. The resultant thermally elevated amalgam of denatured proteins bind together to create a biological weld. When the source of thermal energy is removed, the proteins re-nature and fuse the luminal walls. As the vessel heals over time, the biological weld is reabsorbed by the body via the wound healing process.

Several variables come into play when using RF energy to elevate luminal tissues to the levels required to denature proteins. For purposes of the present invention, the energy source may be a previously known RF generator operating with a high frequency alternating current (e.g., from 50,000 Hz to 550,000 Hz) that is adapted to flow from (or between) one or more electrodes through the vessel walls targeted for welding. As is known, the application of such alternating current causes ionic agitation and friction in the targeted tissue as ions (generally within extracellular matrices and not within intracellular fluids) follow the changes in direction of the alternating current. Such ionic agitation or frictional heating does not result from direct tissue contact with a resistive electrode.

In the delivery of energy to a tissue mass, I=E/R, where I is the intensity of the current in amperes, E is the energy potential measured in volts and R is the tissue resistance measured in ohms. Current density, or the level of current intensity, is an important gauge of energy delivery, and relates to the impedance of the targeted tissue mass. The level of heat generated within the target tissue thus is influenced by several factors, such as (i) RF current intensity, (ii) RF current frequency, (iii) impedance levels within the targeted tissue disposed between the electrodes, which vary during a treatment cycle, (iv) heat dissipation from the targeted tissue; (v) duration of RF energy delivery, and (vi) distance traveled through the targeted tissue by the RF current between the conductive electrodes.

Figure 2A:
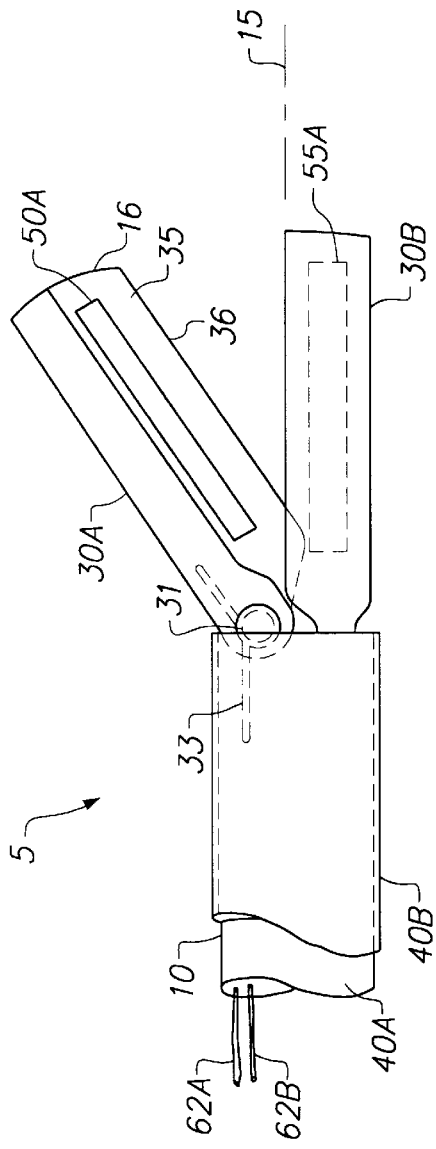
FIGS. 2A–2B are, respectively, plan views of the jaw structure of a first family of embodiments of the present invention with the jaw sides in the open and closed positions.
Figure 2B:
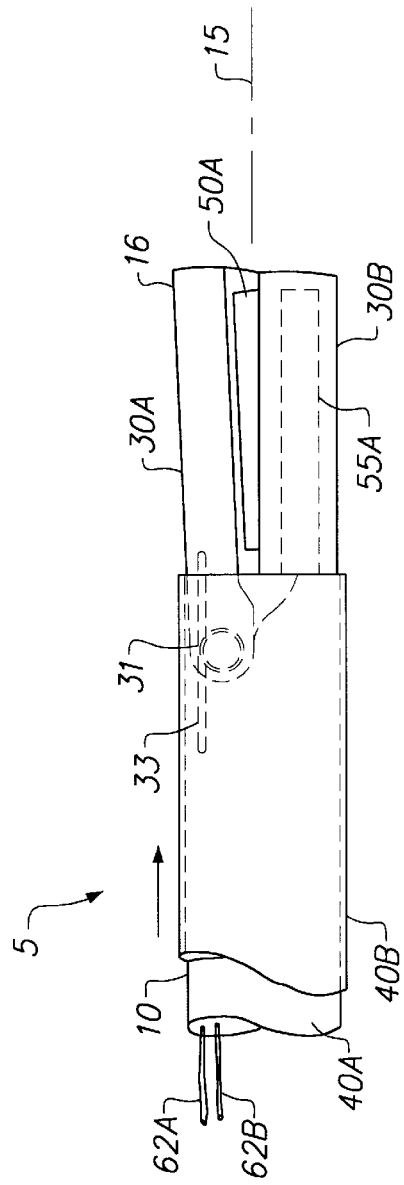

Referring now to FIGS. 2A–2B, a member of a first family of preferred embodiments constructed in accordance with the present invention is described. Instrument 5, which is adapted for open or endoscopic procedures with handle portion 7 (see FIG. 6A), is coupled to elongate introducer portion 10 extending along axis 15 and carrying distal working end 16. Introducer portion 10 illustratively has a cylindrical cross-section and is made of suitable biocompatible materials, such as metal or plastic. Introducer portion 10 preferably has an outer diameter ranging from 5 mm to 10 mm, e.g., to cooperate with a standard endoscopic trocar sleeve.

Figure 3A:
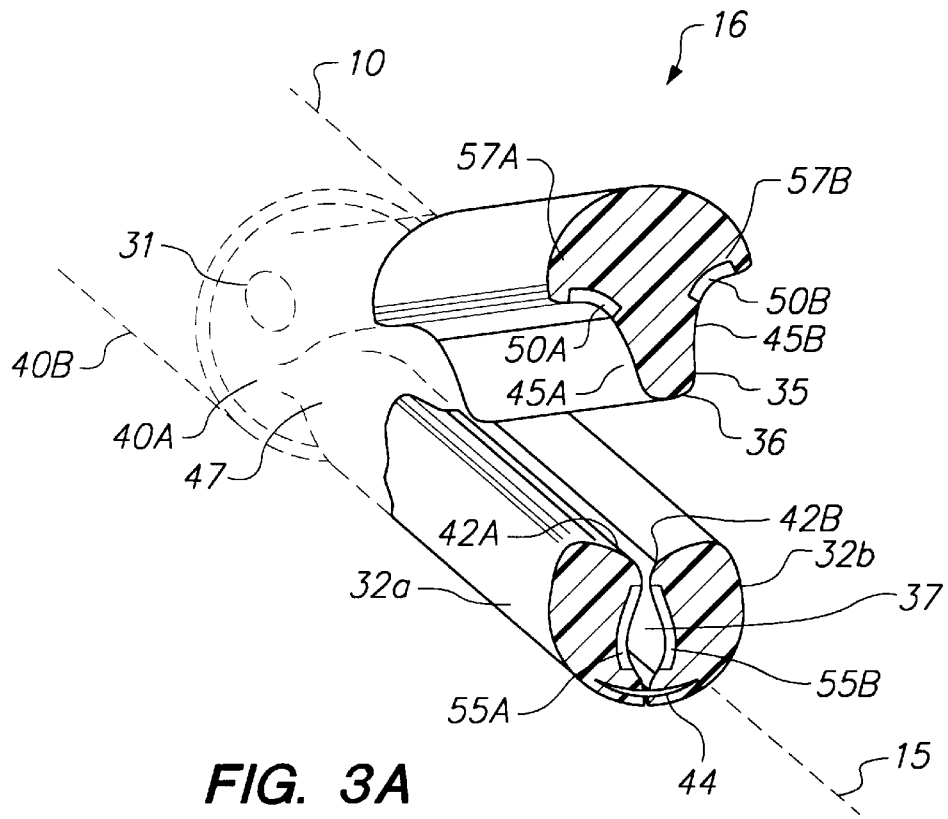
FIG. 3A is a perspective sectional view of the jaw structure of FIG. 2A.
Figure 3B:
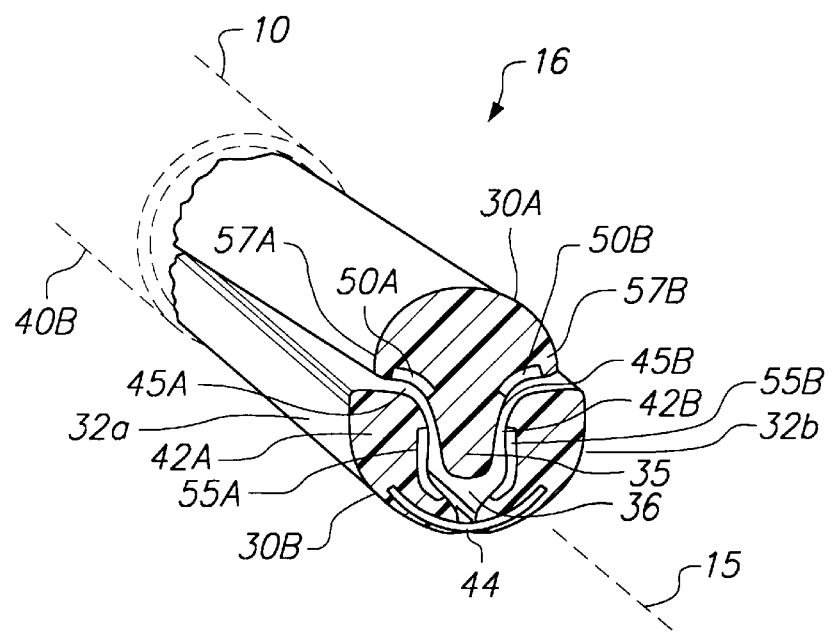
FIG. 3B is a perspective sectional view of the jaw structure of FIG. 2B.
Figure 4A:
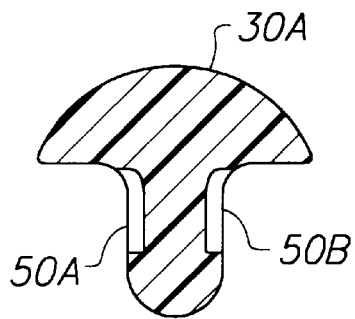
FIGS. 4A–4D depict alternative cross-sectional shapes of the upper jaw side of the device of the present invention.
Figure 4B:
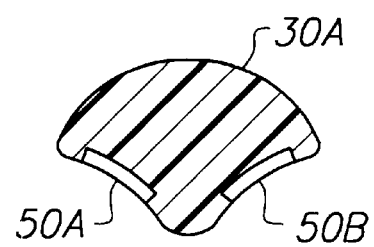
Figure 4C:
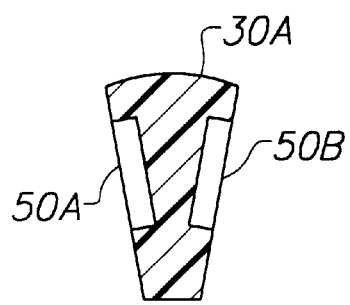
Figure 4D:
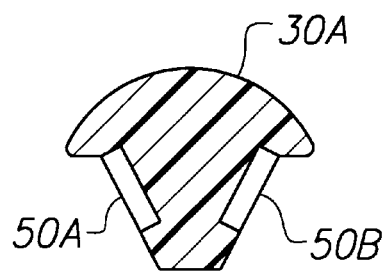

Referring now also to FIGS. 3A–3B, working end 16 comprises an openable/closeable jaw assembly with first and second jaw sides or members 30A and 30B carried by introducer portion 10. Upper jaw side 30A is pivotable around pin 31 and lower jaw side 30B is in an axially stationary position relative to the introducer member. Alternatively, both jaw arms or members 30A and 30B may be pivotable.

Lower jaw member 30B is configured as resilient structure with right-side and left-side jaw elements 32a and 32b (when viewed from the proximal end of instrument 5) defining space or gap 37 therebetween. The deflectable right-side and left-side elements 32a and 32b are adapted to at least partly straddle the centered projecting portion 35 of upper jaw side 30A when closing. Upper jaw member 30A is moveable relative to lower jaw member 30B from an open position (shown in FIGS. 2A and 3A) through various converging positions (not shown) towards the closed position of FIGS. 2B and 3B. Spring 33 biases jaw member 30A to the open position (see FIG. 2A and 2B).

Introducer portion 10 comprises concentric inner and outer extension members 40A and 40B. Lower jaw side 30B extends from inner extension member 40A and upper jaw side 30A is pivotably coupled to inner extension member 40A by pivot pin 31. Outer extension member 40B slidably cooperates with inner extension member 40A and serves as a jaw-actuation mechanism to slidably push the upper jaw toward a closed position (FIG. 2B). Alternatively, upper jaw 30A may be coupled to extension member 40A by any suitable form of resilient hinge-type element rather than pivot pin 31, such as a living hinge formed of plastic injection-molded material. Upper and lower jaw members 30A and 30B of working end 16 are of a medical grade plastic or other nonconductive material or are otherwise insulated from the RF electrodes carried within the jaw assembly which are described in more detail below.

Lower jaw side 30B comprises right-side jaw face portion 42A and left-side jaw face portion 42B on deflectable elements 32a and 32b, respectively, which elements are capable of deflecting or flexing rotationally relative to axis 15. Each right-side and left-side jaw face 42A and 42B optionally may have a grip texture 43 (not shown which may include serrations, hatching, projecting points, etc.) covering its vessel-engaging surface for gripping an engaged vessel.

As may be observed by comparing FIG. 3A and FIG. 3B, each of deflectable jaw elements 32a and 32b rotationally flexes about spring hinge element 44. Hinge element 44 may be a flat spring of any suitable resilient material, and urges the top edges of elements 32a and 32b inward toward axis 15. Alternatively, elements 32a and 32b may be pivotable relative to axis 15 by means of a pin-type hinge (not shown) with a spring urging the arm inward toward axis 15, rather than employing hinge element 44. Elements 32a and 32b are coupled to extension member 40A by resilient connections at 47 disposed in the distal end of extension member 40A. In a preferred embodiment, plastic elements 32a and 32b are engaged with insert-molded metal hinge element 44.

In operation, when right-side and left-side jaw faces 42A and 42B close toward the proximal-most edge 36 of cooperating projecting portion 35, and thereafter push against edge 36, deflectable elements 32a and 32b deflect rotationally outwardly. This movement of elements 32a and 32b in turn causes faces 42A and 42B to slide along right-side face 45A and left-side face 45B, respectively, of projecting portion 35. The axial force required to be applied on extension member 40A to cause elements 32a and 32b to deflect around projecting portion 35 is not high, and is determined by the spring constant of the resilient material of hinge element 44.

The spring material of hinge element 44 preferably is selected to provide sufficient resistance to outward deflection of elements 32a and 32b to collapse a blood vessel and then to maintain a length of the captured vessel under pressure, thereby insuring the walls of the vessel lumen are in suitable contact for welding. Thus, cooperation of right-side and left-side faces 42A and 42B when sliding around right-side and left-side faces 45A and 45B, respectively, of projecting portion 35 progressively engages the vessel, from its center outward, to squeeze blood from the lumen. Moreover, cooperation of right-side and left-side faces 42A and 42B when sliding around right and left-side faces 45A and 45B stretches the vessel section around projecting portion 35. The extent of such stretching or vessel elongation is partly dependent on the grip texture 43 (not shown) impressed on right-side and left-side faces 42A and 42B and the resistance to flexing engineered into hinge element 44 coupling elements 32a and 32b.

Referring still to FIGS. 3A and 3B, the cross sectional shape of projecting portion 35 has an arcuate shape with right-side and left-side face portions 45A and 45B that extend into gap 37 between elements 32a and 32b and the cooperating curved surfaces thereof. Cooperating faces 42A and 42B and 45A and 45B, respectively, may be have any suitable planar or curved cross-section relative to one another, and still squeeze the blood from the lumen as a blood vessel is collapsed. FIGS. 4A–4D depict alternative cross-sectional shapes of distal jaw side 30A of an openable/closeable jaws structure having projecting portion 35. The cooperating lower jaw side 30B (not shown) for the upper jaw 30A depicted in FIGS. 4A–4D would include a curved or linear mating surface for surfaces 45A and 45B.

Working end 16 carries an active and non-active electrode configuration that allows RF energy delivery at very low power levels, e.g., 0.50 to 30.0 watts, as described hereinbelow, yet still creates thermal effects in tissue sufficient to denature proteins. The electrode configuration performs a method of RF energy delivery referred to herein as "directed-path" bi-polar RF energy delivery. Such "directed-path" RF energy delivery is accomplished using a "channeling" electrode system comprising at least one "non-active" electrode that is positioned in contact with the targeted tissue, but spaced apart and intermediate to the first and second "active" bi-polar electrodes.

In FIGS. 3A–3B, right-side and left-side faces 45A and 45B, respectively, of projecting portion 35 carry cooperating right-side and left-side active bi-polar electrodes 50A and SOB. As shown in FIGS. 2A and 2B, wires 62A and 62B carry bi-polar RF energy to and from the paired conductive electrodes 50A and 50B. Active electrodes 50A and SOB may comprise any suitable material, such as gold, nickel titanium, platinum, stainless steel, aluminum or copper, and may be molded or bonded to faces 45A and 45B of the upper jaw member. Channeling electrodes 55A and 55B are carried in right-side and left-side jaw faces 42A and 42B, respectively, that generally oppose jaws faces 45A and 45B carrying active electrodes 50A and SOB, respectively. Channeling electrodes 55A and 55B may comprise any suitable conductive material, but are not electrically active, i.e., they are entirely surrounded by nonconductive material, such as a plastic.

In accordance with one aspect of the present invention, a channeling electrode may comprise a one or more such electrode. For example, hinge element 44 may comprise a channeling electrode, if in contact with tissue, and thus serve multiple functions. As described hereinbelow, any number of channeling electrodes may be used, provided that the channeling electrodes are proximate to one another and positioned to contact the targeted tissue between the active electrodes. The channeling electrodes of the present invention direct the path of bi-polar RF current flow at the desired low power levels (0.50 to 30.0 watts).

The active electrode pair 50A and 50B are configured to send RF energy through a targeted longitudinal section of vessel captured in working end 16. While right-side and left-side electrodes 50A and 50B are illustratively carried by upper jaw member 30A, it will be appreciated that these electrodes may be carried in any left and right parts of working end 16 in contact with an engaged blood vessel for delivering RF current longitudinally through the vessel section. For example, the electrodes alternatively may be carried in right-side and left-side faces 42A and 42B of jaw elements 32a and 32b. The channeling electrode(s) may be arranged at any suitable position between the left and right active bi-polar electrodes, or may even overlap the active bi-polar electrodes.

Figure 5:
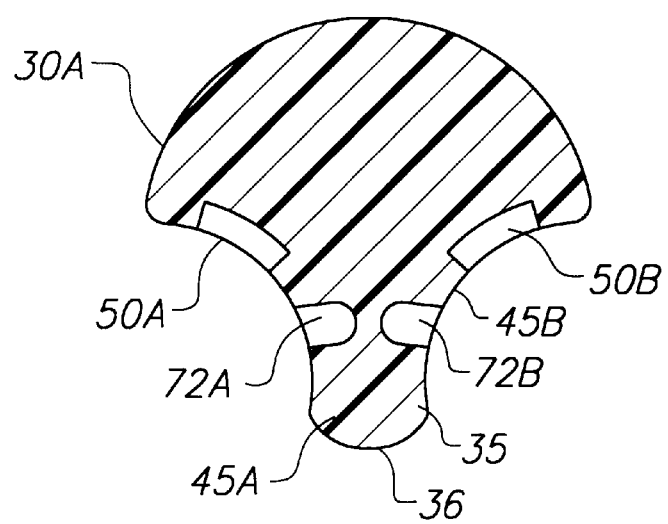
FIG. 5 shows an alternative upper jaw element having thermal sensors.

With respect to FIG. 5, an alternative embodiment is described that includes an array of individual sensors 72A and 72B carried in a portion of the jaw assembly that contacts the blood vessel section being welded. Sensors 72A-72B preferably are located slightly spaced apart from electrodes 50A and 50B, and measure temperatures of tissue adjacent to the active electrodes during a vessel welding operation. Alternatively, sensors 72A and 72B may be replaced by more or fewer sensors, and may be configured to measure the temperatures of the electrodes, rather than the adjacent tissue. Each sensor of an array preferably comprises a thermocouple, e.g., a T-type thermocouple formed from paired dissimilar metals such as copper and constantan, or a thermistor (i.e., a temperature sensor that has a resistance that varies with the temperature level).

Figure 6B:
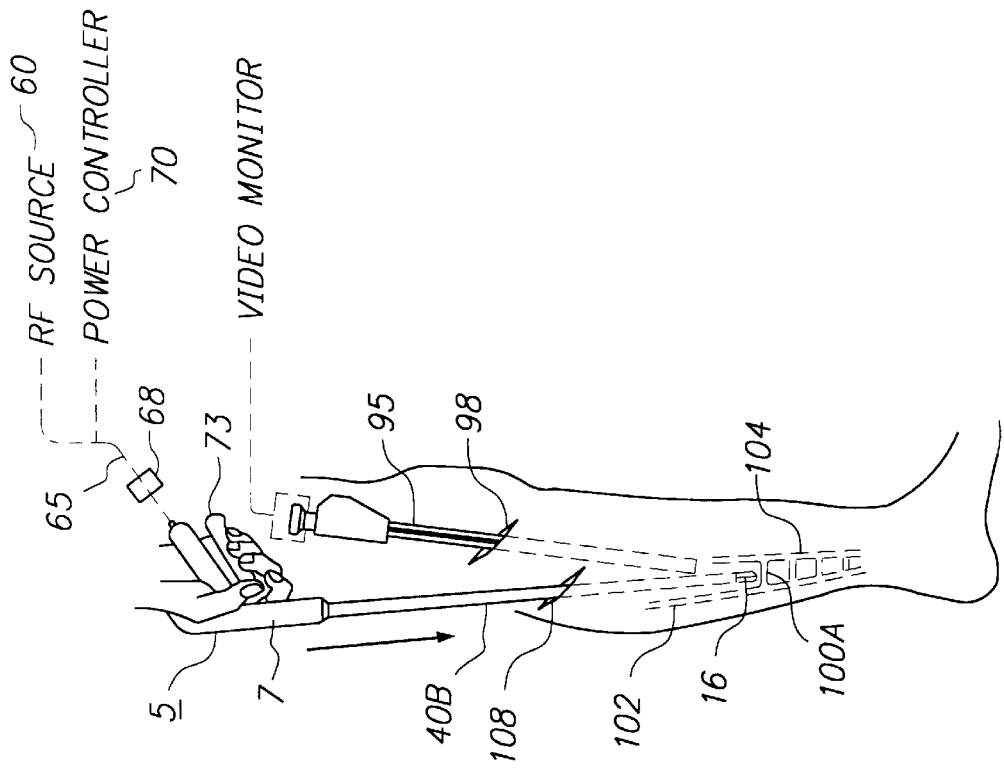
FIGS. 6A–6B are schematic views of a SEPS procedure performed using the instrument and methods of the present invention.
Figure 6A:
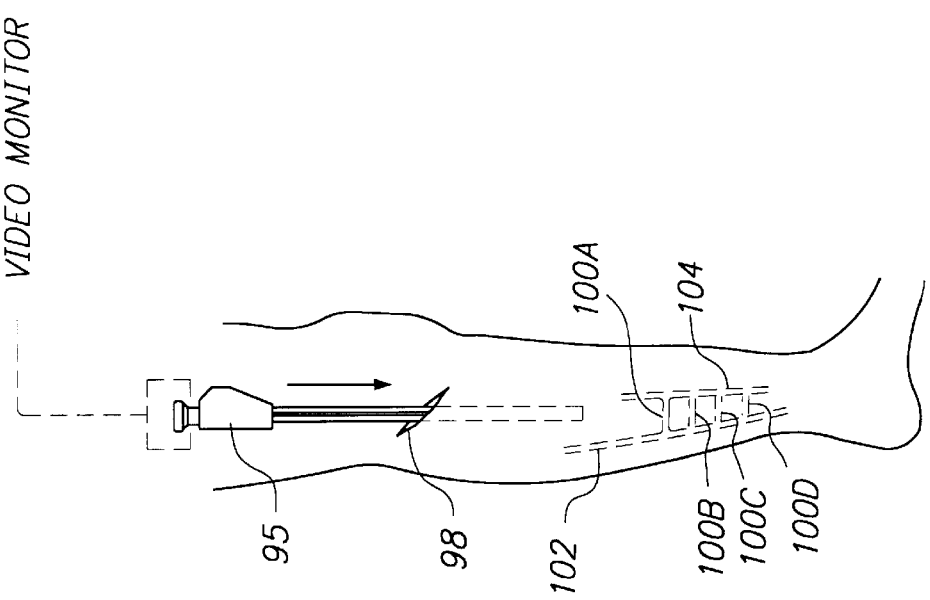

Referring now to FIGS. 6A–6B, RF source or generator 60 is provided for delivering RF current to active bi-polar electrodes 50A and 50B in contact with the blood vessel (or other vascularized tissue) engaged in the jaw assembly. As shown in FIG. 3B, the active and channeling electrodes are positioned in faces 45A–45B and 42A–42B so as to provide laterally outwardly directed insulated portions 57A and 57B of both jaw members, thereby insuring that the electrodes are not exposed on an outermost surface of working end 16 when the jaws are closed. Thus, the positioning of electrodes prevent them from contacting tissue surfaces other than the targeted vessel section.

Bi-polar wires 62A and 62B extend through handle portion 7 (see FIG. 6A) to power transmission cable 65, which is connected via a detachable coupling to an energy source, such as a previously known RF generator or source 60. Bi-polar RF current may be switched on and off by foot pedal 68, or any other suitable means such as a switch in handle 7 (not shown). Optional power controller 70, described in more detail hereinbelow, is coupled to instrument 5 and RF source 60 via cable 65. Lever arm 73 in handle 7 is arranged to move outer extension member 40B back and forth as a jaw-actuating mechanism, as is known in the art, to move upper jaw side 30A toward lower jaw side 30B between the open position (FIG. 2A) and the closed position (FIG. 2B).

Still referring to FIGS. 6A–6B, operation and use of the instrument of FIG. 2 in performing a method of the invention is described. First, the surgeon inserts endoscope 95 (or any other suitable instrument) into a patient's leg through first incision 98, to dissect an access path to perforator 100A between superficial vein 102 and deep vein 104. It should be appreciated that there may be from one to ten or more perforator vessels that must be sealed in a SEPS procedure, four perforators 100A–100D are shown. The surgeon then introduces the distal end of instrument 5 through second incision 108 and advances it towards the location of perforator 100A. The access space around the perforators may be dissected and retracted mechanically or by insufflation by known means (not shown).

Figure 7A:
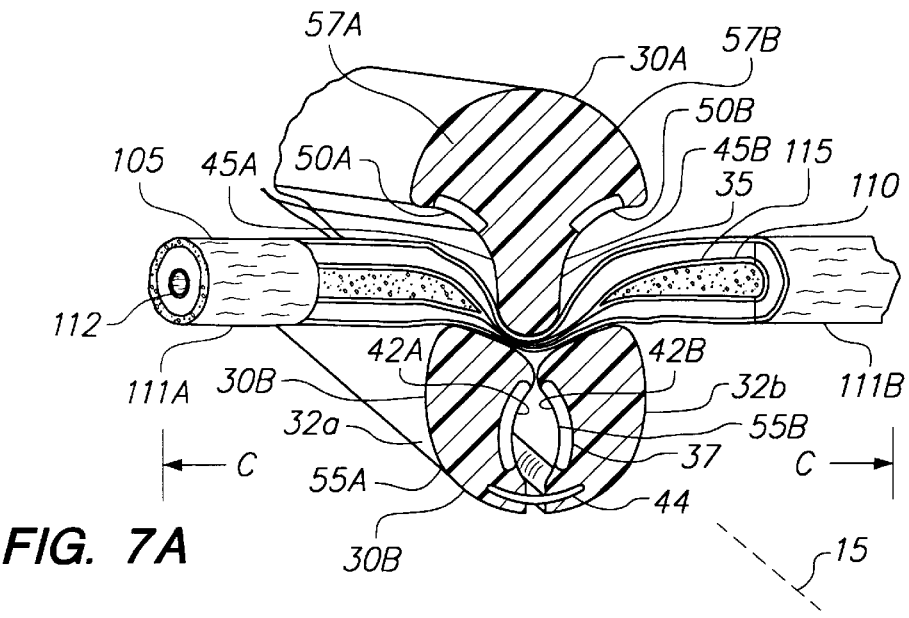
FIGS. 7A–7C are sectional views of a part of a blood vessel targeted for treatment depicting, in sequence, a method of the present invention to weld or seal the blood vessel lumen.

FIG. 7A is an enlarged view representing a particular longitudinal section 105 of perforator 100A (or any other blood vessel) that is targeted for sealing in the interior of the patient's body. The surgeon generally identifies a vessel section 105 which is bounded by right and left end portions 111A and 111B and is positioned between upper and lower jaw members 30A and 30B in the open position. The vessel has lumen 110 and endothelium 112 with blood 115 within. Right and left ends 111A and 111B, respectively, of vessel 105 are spaced apart a distance C, as described further below.

Figure 7B:
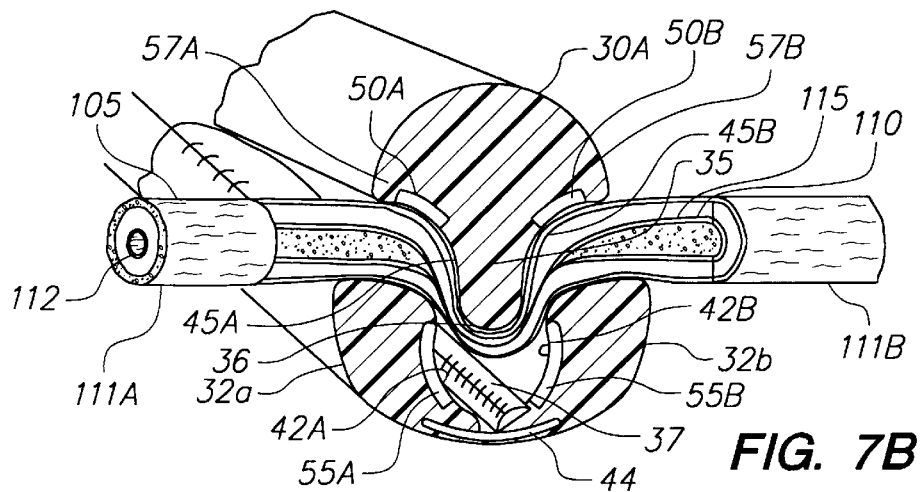

With respect to FIG. 7B, the surgeon progressively moves the jaws toward the closed position, so that right-side and left-side faces 42A and 42B of lower jaw side 30B press and collapse the vessel against proximal-most edge 36 of projecting portion 35. Thus, as lumen 110 is collapsed at a center portion of the targeted vessel section, flow of blood 115 through the vessel is pinched off and terminated.

Figure 7C:
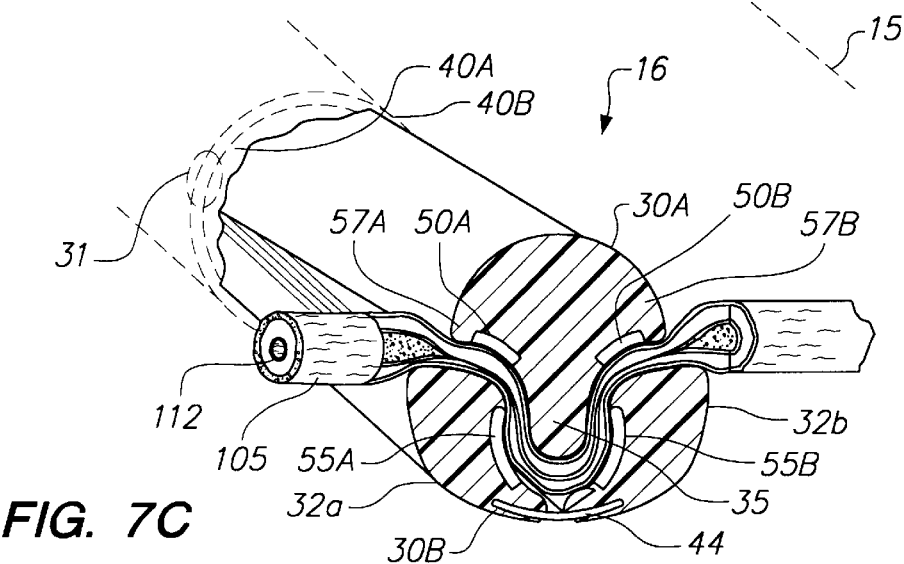

Referring next to FIGS. 7B and 7C, as vessel progressively collapses further, substantially all of the blood is squeezed from the vessel segment targeted for sealing. In particular, right-side and left-side jaw faces 42A and 42B carried by deflectable elements 32a and 32b of the lower jaw structure slidably move over the vessel relative to faces 45A and 45B of opposing jaw side 30A. In contrast to previously known jaw arrangements, which may trap blood between approximated vessel walls, the progressive sliding movement of portions of jaw faces 42A and 42B relative to the opposing jaw faces 45A and 45B causes substantially all blood 115 to be pushed out of the targeted vessel section. FIG. 7C shows the vessel section 105 captured in the jaw assembly in the closed position, ready for RF energy delivery.

Figure 8:
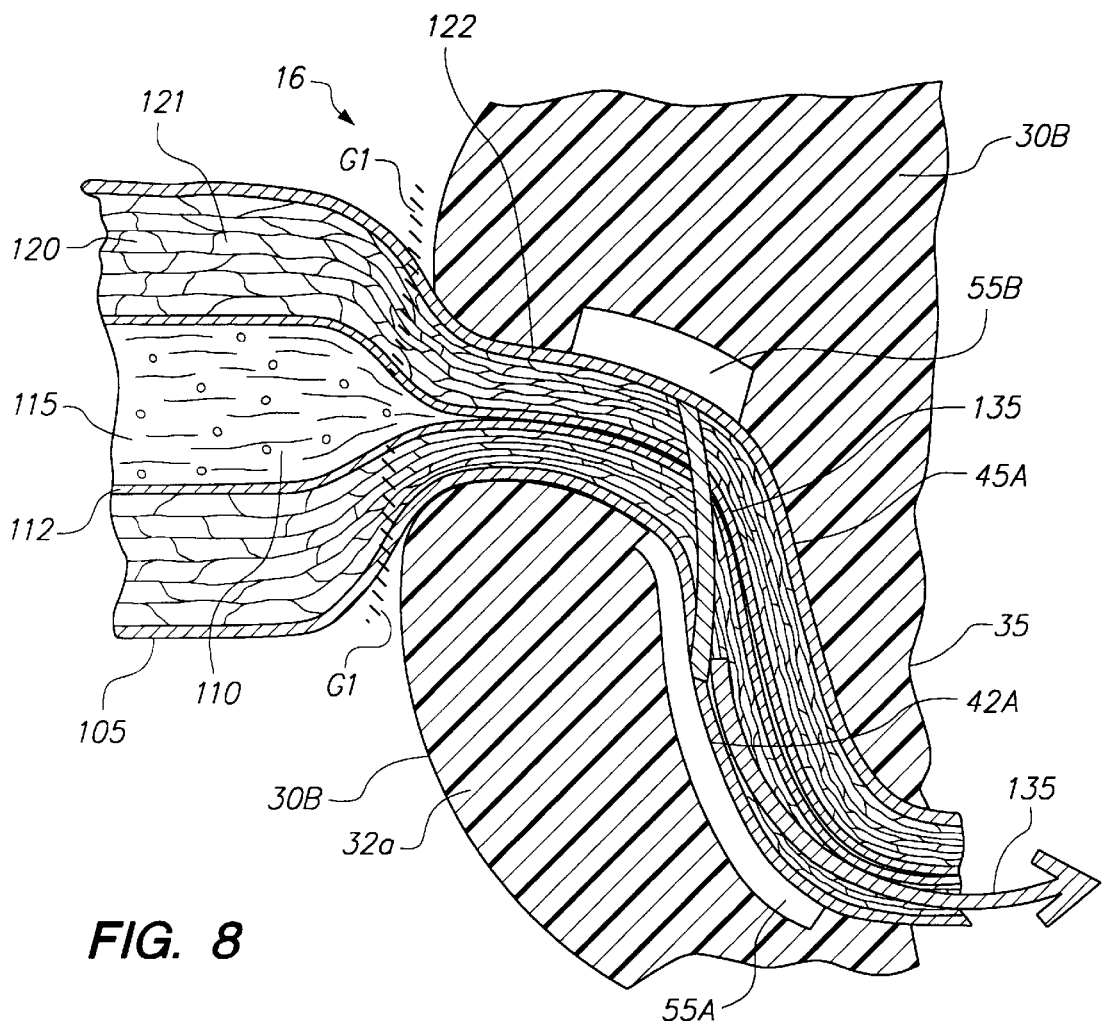
FIG. 8 is a sectional view of the targeted vessel section taken along line 8—8 of FIG. 7C.

Referring now to FIG. 8, an enlarged view of vessel section 105 is shown with RF current flow indicated by arrows 135. To weld or seal the target vessel section, the surgeon actuates a foot pedal or other type of switch to allow a bi-polar current to flow between electrodes 50A and electrode 50B longitudinally through the extended length C' of the vessel. The RF current flow along a path from the first bi-polar electrode, through the most conductive tissue, and to the cooperating second bi-polar electrode, i.e., along the path of least resistance between cooperating electrodes.

Applicant has discovered that by positioning channeling electrodes 55A and 55B intermediate to the active bi-polar electrodes 50A and 50B, RF current flow is channeled or directed between the active electrodes through the tissue in contact with the channeling electrodes. As illustrated in FIG. 8, arrows 135 (collectively) indicate the flow of RF current generally from first bi-polar electrode 50A through tissue toward channeling electrode 55A, then generally longitudinally through tissue proximate to channeling electrodes 55A and 55B, until reaching cooperating bi-polar electrode 50B.

Of particular interest to this method of the invention, it has been found that the use of the channeling electrode system substantially reduces "stray" RF current that finds its way along other paths of lesser resistance through tissues between electrodes. By thus directing RF current along a desired path through the tissue, along with the absence of stray RF flows, it has been observed that RF power levels can be reduced significantly and still deliver the required thermal effects needed to weld tissues.

Accordingly, the present invention provides a method of utilizing a working end 16 that has longitudinally spaced-apart bi-polar electrodes with at least one intermediate channeling electrode, is adapted to deliver RF current ranging in power from 0.50 to 30.0 watts for sealing lumens in organs, the power levels varying depending generally on the size of the vessel being sealed. More preferably, the method will deliver RF current ranging in power from 0.50 to 20.0 watts, and still more preferably, from 0.50 to 10.0 watts, to weld endothelial tissues or collagen containing tissues to create a thermal biological glue.

Referring still to FIG. 8, the schematic sectional illustration shows that an elongate weld 125 is created where the proteins (including collagen) are denatured, then intermix, and then fuse together upon cooling to fuse the vessel walls together. In delivering the flow of RF current generally between electrodes 50A and 50B along the path directed by channeling electrodes 55A–55B, the surgeon may select a pre-set current intensity levels. The duration of RF delivery may range from about 1.0 seconds to about 30.0 seconds or more depending on current intensity.

Returning to FIGS. 7A–7C, another aspect of the methods of the invention is described, in which the targeted vessel section is stretched or elongated as it is engaged by working end 16. In particular, targeted vessel section 105 is stretched somewhat lengthwise when right end 111A and left end 111B move apart, relative to the axis of the vessel. The pre-manipulated length of target section is indicated at C in FIG. 7A. The optional gripping texture 43 (not shown) of right-side and left-side faces 42A and 42B may assist in extending the vessel. It can be seen that the closing action of working end 16 causes projecting portion 35 to extend target vessel section 105 into gap 37 as deflectable elements 32a and 32b straddle projecting portion 35 to extend the vessel. FIG. 7C illustrates that the targeted vessel section is extended or lengthened somewhat to a length indicated at C' from the initial length indicated at C (FIG. 7A).

This aspect of longitudinally stretching or tensioning the vessel prior to RF delivery alters the impedance characteristics of the target tissue, thus enhancing RF energy delivery. Specifically, extension of the target vessel portion in FIG. 7C lowers the extracellular fluid (ECF) content of the vessel walls that are extended, thereby increasing the impedance (or resistance) of the tissue to RF current flow. Additionally, such stretching or tensioning may configured to provide a substantially uniform thickness of the target vessel, thereby ensuring a relatively uniform impedance over the length of the elongated, collapsed section of vessel.

Without limiting the method of the present invention to any particular theory, it is believed that the tissue extension or manipulation has the effect of (1) decreasing the ECF content level of the target vessel section 105 when calculated in terms of ECF/cm² of tissue mass, and (2) making the ECF level more evenly distributed throughout the targeted tissue (at the lower ECF/cm² level) whereas in the prior state, the ECF level could vary randomly within the cellular structure.

In FIG. 8, ECF in the non-extended tissue (indicated at 120) between cells 121 is altered to a different state in the extended tissue (indicated at 122), as the extracellular fluid is squeezed out of the tissue (this is indicted graphically by the varied patterns of cell density in FIG. 8, compare locations 120 and 122). In other words, a hydration gradient G1 is created between the tissue to be treated and the tissue outside the treatment area. In this way, the RF current generally flows through the extracellular matrix rather than passing through the intracellular fluids and cellular membranes.

The effects of the tissue manipulation caused by the extension of targeted vessel section 105 alternatively may be described as causing a "fuse" or "fuse point" to form in the tissue when subjected to the flow of RF current. Several advantages are offered by creating a fuse-type effect in the targeted tissue.

First, the delivery of RF current between electrodes 50A and 50B will deliver greater levels of thermal effects for a given current flow or intensity. Thus, the targeted tissue may be elevated to a particular desired temperature to denature proteins of endothelium 112 at lower levels of RF energy delivery. It is desirable to use lower levels, rather than higher levels, of RF current intensity which, it is believed, will reduce tissue charring, smoke and odor.

Second, the requisite temperature range for protein denaturation can be reached more quickly, thus speeding up the process of tissue welding. These first two advantages provide for an enhanced energy delivery profile (delivery of current intensity over several seconds).

Figure 1B:
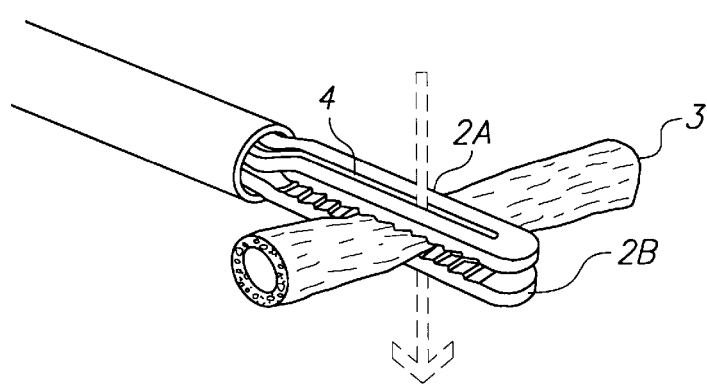
Figure 1C:
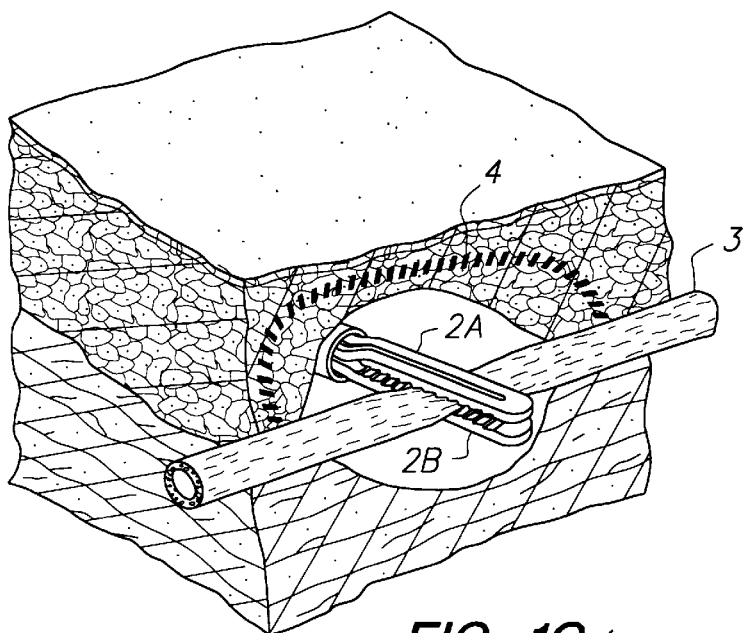

Third, the bi-polar flow longitudinally through the vessel between electrodes 50A to 50B naturally denatures proteins over a longer length of vessel lumen, thereby creating a more effective seal. This effect is not possible with typical prior art bi-polar devices that send current through pinched tissue between opposing jaw-electrodes (see FIG. 1B).

Fourth, it is believed that the uniformity in the ECF level in the target tissue allows for more uniform denaturation to provide a uniform biological glue.

Fifth, the bi-polar current flow longitudinally through the vessel provides little or no thermal spread outwardly along the vessel, since the RF current substantially flows along the path directed by the channeling electrodes between the paired "active" electrodes (and not outwardly). Also, the higher ECF level indicated at 120 in the vessel outwardly from vessel ends 111A and 111B, together with blood 115, acts as a heat sink to prevent significant outward thermal spread. In addition, the insulator portions of the working end 57A and 57B, outward of electrodes 50A and 50B, also prevent outward thermal spread.

Figure 9:
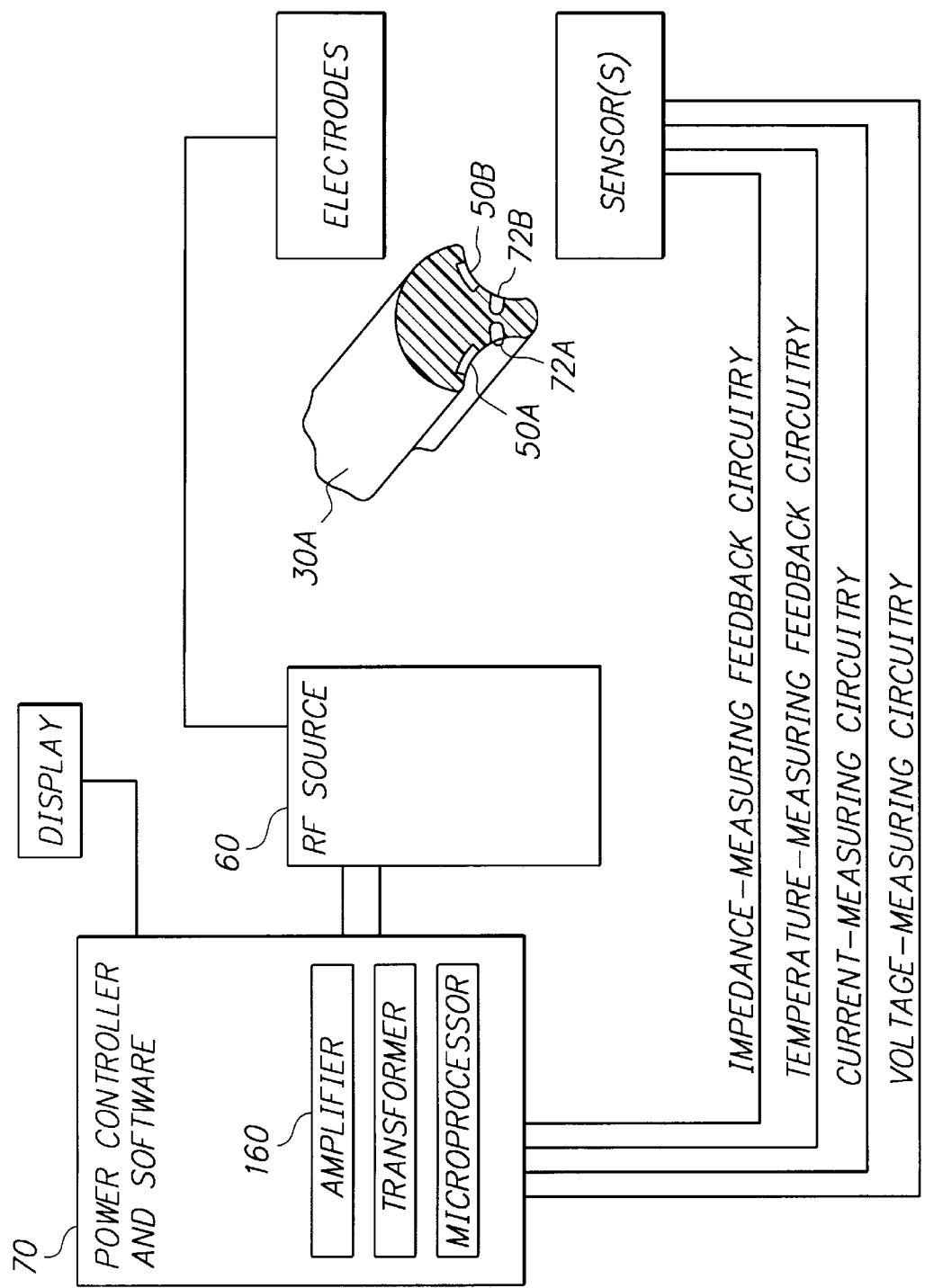
FIG. 9 is a block diagram of a power controller of an alternative embodiment of the apparatus of the present invention.

Referring now to FIG. 9, an alternative embodiment of the present invention is described that includes sensors 72A–72B carried by the working end 16 (as shown in FIG. 5) in combination with electronic power controller 70 indicated in FIGS. 6A–6B. Sensors 72A–72B are adapted to send feedback signals to power controller 70, which modulates the delivery of RF energy delivery to the instrument. Power controller 70 is shown in FIG. 9 interconnecting RF source 60 and instrument 5.

Power controller 70 is adapted to control delivery of RF power in a bi-polar manner between paired electrodes 50A and 50B, as channeled by channeling electrodes 55A–55B according to predetermined parameters. The power controller 70 may be designed to selectively control power delivery to the electrodes in varied operational modes. The power controller 70, which typically includes microprocessor 160 together with appropriate software, may be programmed to deliver power according to preset parameters. On the power controller 70, there may be a keyboard, disk drive or other non-volatile memory system, and displays as are well known in the art for operating the system. Operator interface 162 may include various types of imaging systems for observing the RF treatment cycle such as thermal sensor displays and/or impedance monitoring displays.

In the preferred manner of operation or temperature-controlled operational mode, the operator selects a target temperature level, typically a known temperature at which proteins will denature in the targeted vessel lumen. Temperature signals measured by a sensor or sensor array 72A and 72B are continuously provided to power controller 70 through a feedback circuit. Power controller 70 is programmed to terminate power delivery after the targeted vessel section reaches a predetermined temperature for a sufficient period of time, e.g., from about 1.0 second to about 30.0 seconds, to denature proteins and form a biological glue but still not carbonize the tissue.

The temperature at the surface of the vessel in contact with the sensors is substantially close to the temperature within the lumen. RF power source 60 delivers RF current ranging in power at the aforementioned power levels for the time intervals above to reach (or maintain) tissue temperatures ranging between 65° C. and 95° C. to denature proteins in the (collagen-containing) endothelial tissues to form a biological glue. More preferably, the RF power source delivers RF current ranging under the aforementioned parameters to reach (or maintain) tissue temperatures ranging between 70° C. and 90° C., and still more preferably 75° C. and 85° C., to denature proteins in the endothelial tissues to form the biological glue.

Alternatively, sensors 72A and 72B may be configured to measure tissue impedance, and power controller 70 may include feedback circuitry to modulate RF power delivery to the electrode array based on measured values of tissue impedance. As a yet further alternative, power controller 70 may be configured to estimate energy delivered to the tissue (e.g., based on the voltage between the electrodes and measured RF current) and to regulate the supply of RF current to the electrodes responsive to the estimated energy delivery. Still further, a combination of such operational modes may be employed to regulate energy delivery to the tissue.

Figure 10:
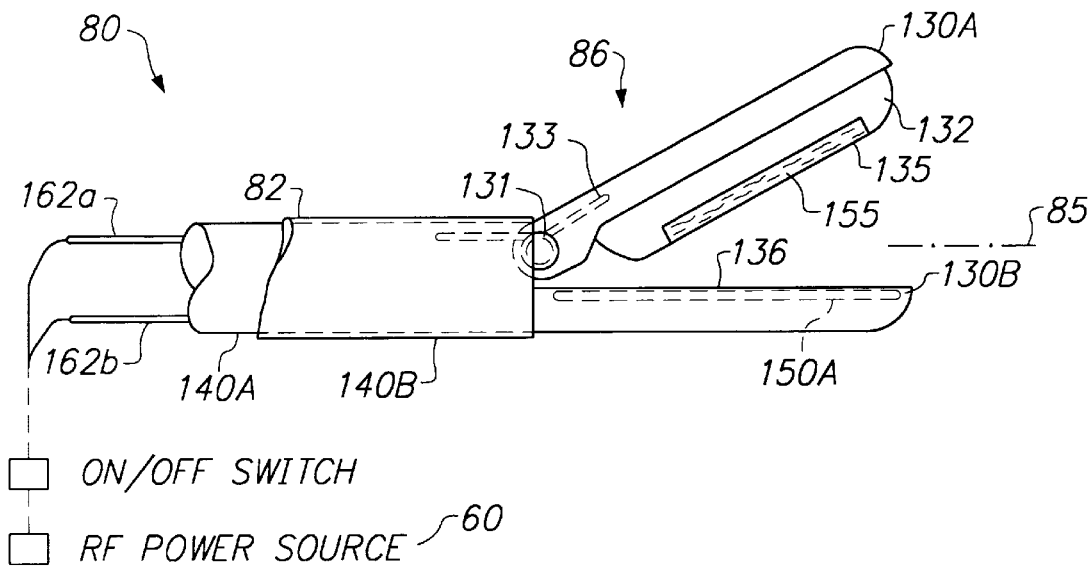
FIG. 10 is a plan view of the jaw structure of a second family of embodiments of the present invention with the jaw sides in the open position.
Figure 11:
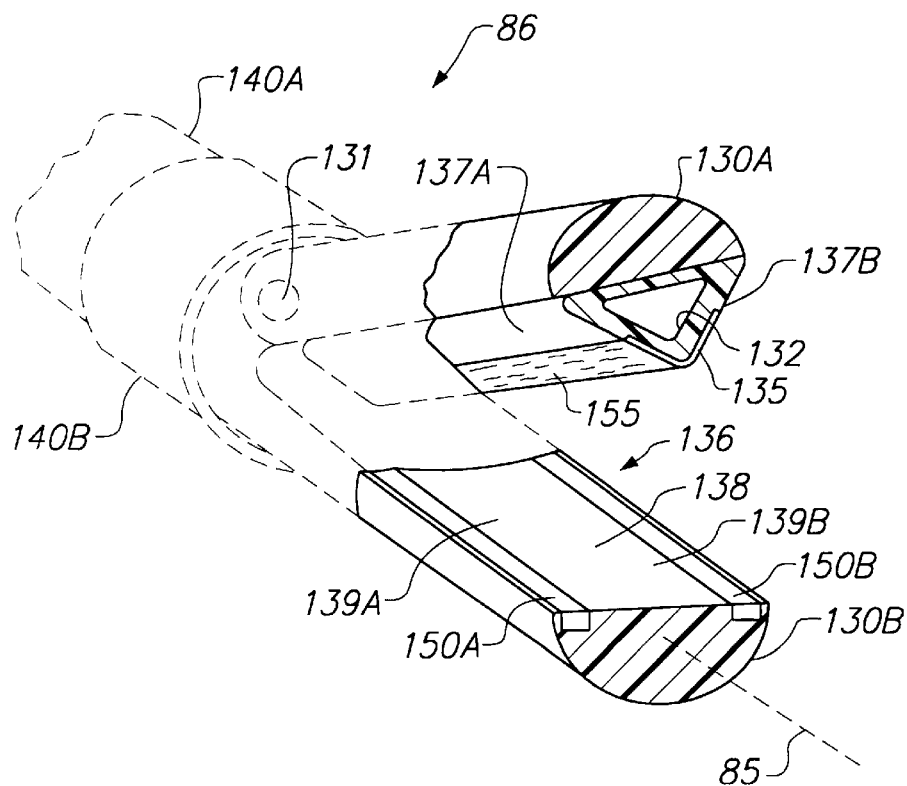
FIG. 11 is a perspective view of the jaw structure of FIG. 10.

Referring now to FIGS. 10 and 11, a first member of a second family of preferred embodiments is described. Instrument 80, like the embodiment of FIGS. 2A–2B, is adapted for open or endoscopic procedures with a handle portion (not shown) coupled to elongate introducer portion 82 extending along axis 85 and carrying distal working end 86. Introducer portion 82 preferably is constructed similarly to the embodiment of FIGS. 2A–2B.

As shown in FIG. 11, working end 86 comprises an openable-closeable jaw assembly with jaw sides or members 130A and 130B carried by introducer portion 82. Upper jaw side 130A is pivotable around pin 131 and lower jaw side 130B is a unitary end portion of the introducer member. Alternatively, both jaw members 130A and 130B may be pivotable. Spring 133 urges jaw side 130A to the open position. Introducer portion 82 preferably comprises concentric inner and outer extension members 140A and 140B formed of electrically insulating material, and may be constructed as described with respect to extension members 40A and 40B of the embodiment of FIGS. 2A–2B.

In accordance with the second family of embodiments of the present invention, upper jaw member 130A includes resiliently deformable jaw element 132, which comprise any suitable elastomeric material, such as rubber. Jaw element 132 has a repose cross-section including a central projecting (or crowned) portion 135 capable of engaging a central portion of a length of targeted vessel. Central projecting portion 135 is configured to progressively deform, shown in FIGS. 12A–12C, as the jaws close together.

More particularly, central projecting portion 135 is configured to meet a central longitudinal portion of lower jaw member 130B and then progressively flatten against engagement surface 136 of the lower jaw. Right-side and left-side portions 137A and 137B of jaw element 132 lie on either side of the axially-extending central portion 135. Engagement surface 136 of lower jaw 130B may have any flat or crowned surface so long as it meets jaw element 132 in such a way as to push blood from the vessel lumen outwardly, as described hereinabove for the first family of embodiments.

Lower jaw member 130B includes an upper surface 136, defining a vessel engagement surface or plane, having center portion 138 and right-side and left-side portions 139A and 139B on either side thereof. Right-side and left-side portions 139A and 139B of lower jaw member 130B carry cooperating right-side and left-side active bi-polar electrodes 150A and 150B. Active electrodes 150A and 150B may comprise any suitable material such as gold, nickel titanium, platinum, stainless steel, aluminum or copper and may be molded or bonded to face portions 139A and 139B of the lower jaw member. Individual current-carrying wires 162a and 162b extend through introducer 82 and couple electrodes 150A and 150B to RF source 60 via a cable.

Optionally, jaw element 132 may include a channeling electrode 155, for example, in the form of a thin electrically conducting film, e.g., comprising aluminum or copper. Alternatively, the elastomeric material forming jaw element 132 may include, for example, a dispersion of silver particles that make the channeling electrode conductive. As for the first family of embodiments, channeling electrode 155 is not directly coupled to the RF source, but only indirectly coupled to the active electrodes through an intervening thickness of tissue.

Channeling electrode 155 preferably is disposed, for example, over a center portion of jaw element 132 intermediate active electrodes 150A and 150B and in opposition to jaw surface 136. Accordingly, when jaw element 132 is closed against a targeted vessel section, the channeling electrode is disposed intermediate to (and depending upon how closely the vessel walls are approximated, even overlapping) active electrodes 150A and 150B to direct the flow of RF current between electrodes 150A and 150B and through the tissue in contact with the channeling electrode.

Figure 12A:
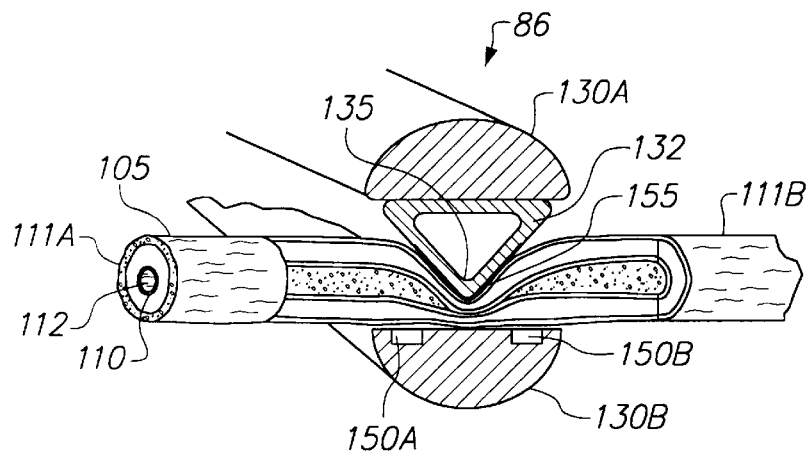
FIGS. 12A–12C are sectional views of a part of a blood vessel targeted for treatment depicting, in sequence, a method of the operating the device of FIGS. 10 and 11.
Figure 12B:
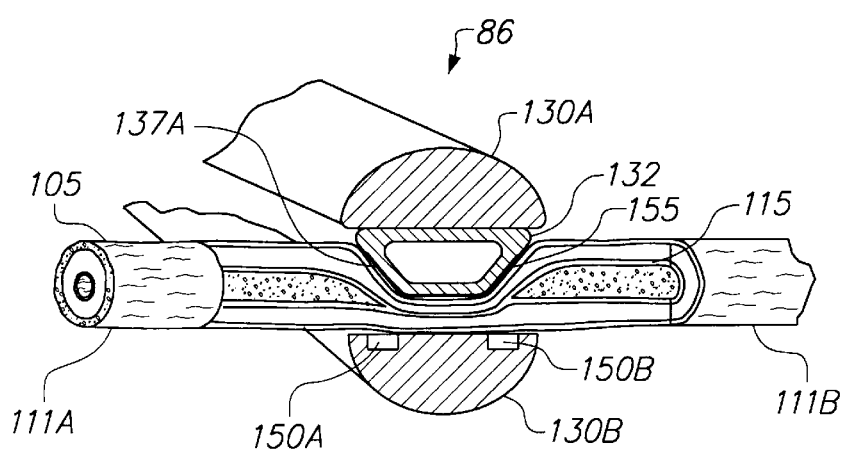
Figure 12C:
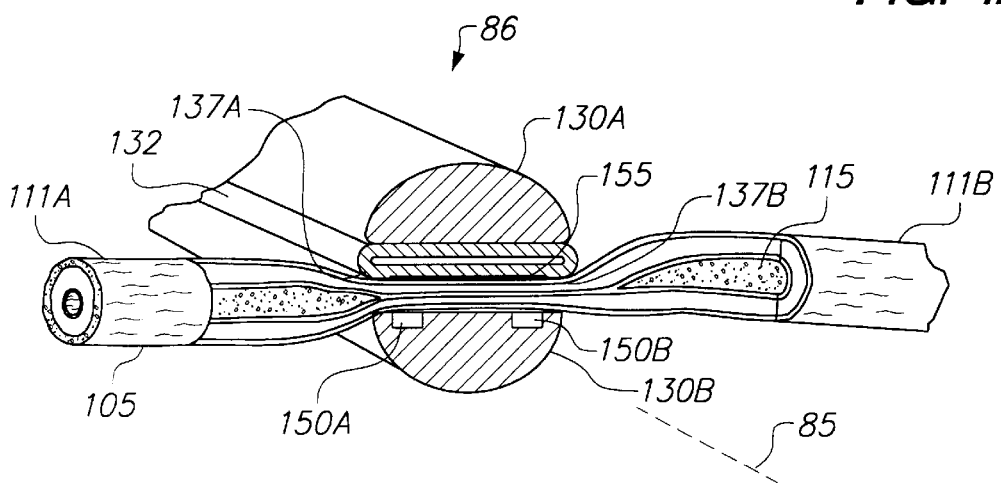
Figure 13:
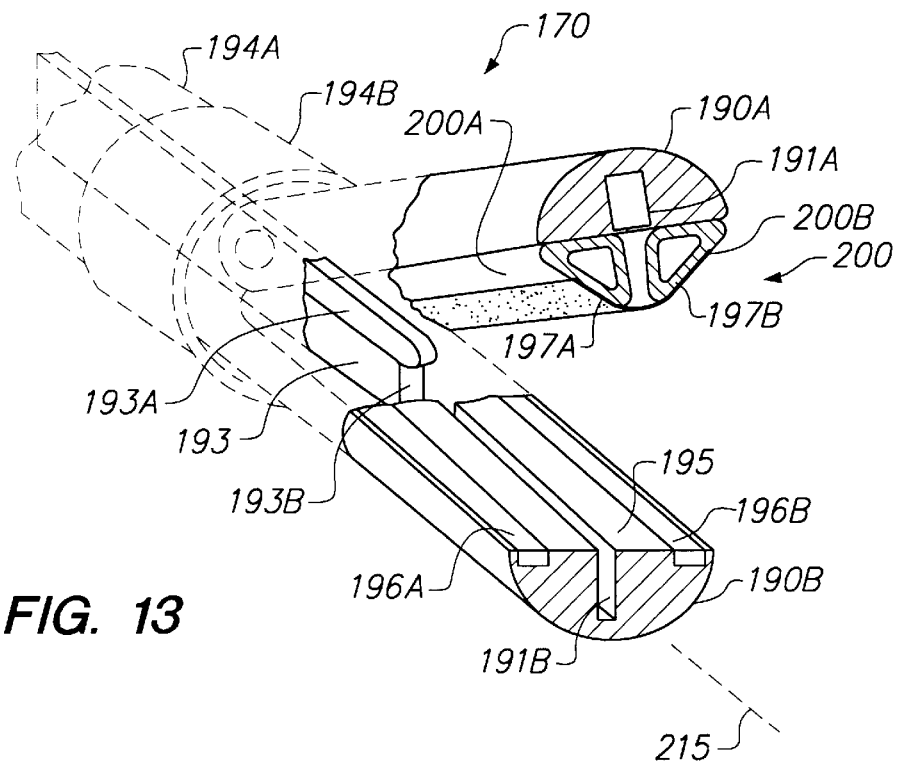
FIG. 13 is a perspective view of the jaw structure of an alternative member of the second family of embodiments of the present invention with the jaw sides in the open position.

Referring now to FIGS. 12A–12C, a method of using instrument 80 of FIGS. 10 and 11 to seal a vessel, illustratively a perforator vessel such as described with respect to FIGS. 6 and 7, is described. In FIG. 12A, section 105 of a perforator vessel (or any other vessel) targeted for sealing is bounded by right and left end portions 111A and 111B, and is positioned between upper and lower jaw members 130A and 130B. Vessel 105 has lumen 110 with endothelium 112 and blood 115 flowing therethrough.

In FIG. 12B, the surgeon progressively moves the jaws 130A and 130B together towards a closed position. Right-side and left-side faces 137A and 137B of the resiliently deformable jaw element 132 collapse as central projecting portion 135 presses vessel 105 against engagement surface 136 of lower jaw member 130B. Thus, lumen 110 at a center portion of the targeted vessel section collapses and the flow of blood 115 through the vessel is pinched off and terminated.

In FIGS. 12B and 12C, vessel 105 is shown being progressively collapsed from the center towards ends 111A and 111B, thereby pushing substantially all blood outward from the vessel section 105 targeted for sealing, and reducing the risk that blood trapped between the approximated vessel walls will interfere with the sealing process. FIG. 12C shows vessel section 105 captured in the jaw assembly in a closed position suitable for RF energy delivery. The surgeon then actuates a switch (not shown) so that an RF current flows between electrodes 150A and 150B, and is directed by channeling electrode 155 to seal the vessel, as described hereinabove with respect to FIG. 8.

While channeling electrode 155 is expected to provide optimal performance, significant improvement still may be achieved in welding vessel 105 closed (although with slightly higher power), even in the absence of channeling electrode 155. This is so because the progressive deformation of jaw element 132 as it closes against lower jaw member 130B squeezes the blood out of lumen 110. Also, that same progressive deformation of jaw element 132 applies a tensile load to the engaged vessel section, thereby stretching that section of the vessel and reducing the level of extracellular fluid in the collapsed vessel section. This in turn creates a high impedance fuse point in the targeted vessel section and provides the various advantages described hereinabove.

Referring now to FIGS. 13 and 14A–14C, an alternative member of the second family of embodiments is described. Instrument 170 is constructed similarly to instrument 80 of FIGS. 10 and 11, except that upper jaw member 190A has a longitudinally divided crowned-shaped jaw element 200 having resilient right side member 200A and resilient left side member 200B. Axial slots 191A, 191B are provided in upper jaw member 190A and lower jaw member 190B, respectively, to accommodate reciprocating blade 193. Reciprocating blade 193, which may be actuated by any suitable mechanism in a handle portion, preferably includes thick portion 193A that is adapted to slide between the resilient side members 200A and 200B to prevent blade edge 193B from cutting, or being dulled by contact with, the resilient side members.

Extension members 194A and 194B are adapted to open and close upper jaw 190A relative to lower jaw 190B as described previously. Lower jaw member 190B includes engagement surface 195 having active electrodes 196A and 196B exposed thereon. Channeling electrodes, 197A and 197B are disposed on right side member 200A and left side member 200B, respectively.

Figure 14A:
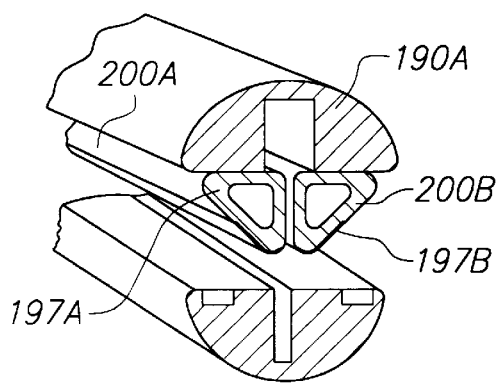
FIGS. 14A–14C are sectional views of a part of a blood vessel targeted for treatment depicting, in sequence, operation the device of FIG. 13.
Figure 14B:
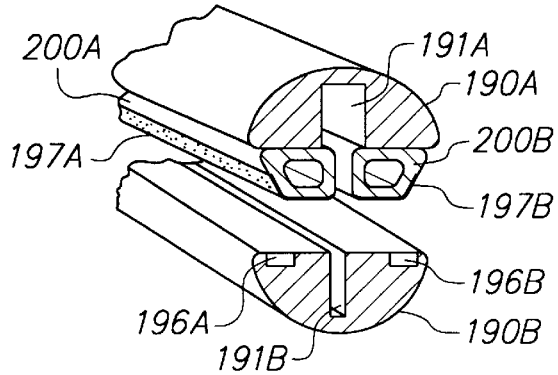
Figure 14C:
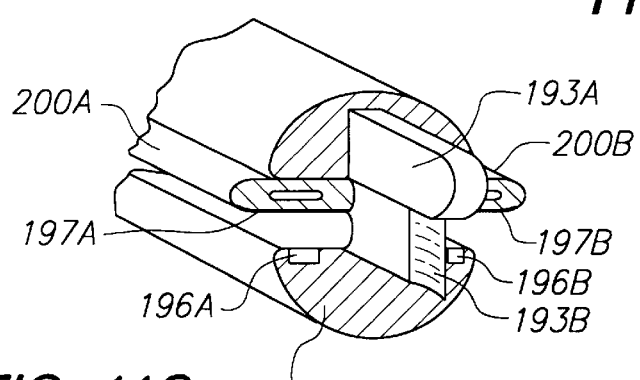

Referring to FIG. 14A, upper and lower jaw members 190A and 190B may be disposed around a vessel (not shown) so that as jaw element 200 closes along central axis 215, right and left side resilient side members 200A and 200B progressively squeeze blood out of the lumen of the vessel in the same manner as jaw element 132 of the embodiment of FIGS. 10 and 11. In FIG. 14B, channel electrodes 197A and 197B direct flow of a bi-polar RF current along engagement surface 195 between right and left electrodes 196A and 196B, as previously described. Upon completion of the vessel welding process, the RF current is terminated, and, as shown in FIG. 14C, blade 193 is advanced in axial slots 191A and 191B to sever the welded vessel.

The present invention may be readily adapted for use in sealing other organs or anatomic structures having a lumen surrounded by walls containing proteins, for example collagen, that may be denatured and intermixed to form a thermal biological glue. It is believed that most tubular organs in the body have walls that are capable of such RF welding utilizing the techniques disclosed herein. For example, various lumens in a patient's body may be sealed such intestines, ducts, and any other tubular organs or conduits in a patient's body.

Although particular embodiments of the present invention have been described above in detail, it will be understood that this description is merely for purposes of illustration. Specific features of the invention are shown in some drawings and not in others, and this is for convenience only and any feature may be combined with another in accordance with the invention. Further variations will be apparent to one skilled in the art in light of this disclosure and are intended to fall within the scope of the appended claims.

What is claimed is:

1. Apparatus for welding a vessel comprising:

a first member having a first vessel engaging surface;

a second member having a second vessel engaging surface, the second vessel engaging surface disposed in opposing relation to the first vessel engaging surface, the second member operatively coupled to the first member to engage a portion of the vessel to define an engagement plane;

means for elongating the portion of the vessel when the first member and second member close towards one another, the means for elongating progressively engaging the vessel to squeeze fluid out of the portion of the vessel disposed between the first and second members; and first and second bi-polar electrodes disposed in spaced apart relation on one of the first and second members and adapted to be in communication with the engagement plane, the first and second bi-polar electrodes adapted to be coupled to a source of RF energy to provide a flow of current between the first and second bi-polar electrodes.

2. The apparatus of claim 1 wherein the engagement plane defines a curvilinear surface.

3. The apparatus of claim 1 wherein the first member forms a mating surface to the second member.

4. The apparatus of claim 3 wherein the first and second members comprise first and second opposing jaw members, the apparatus further comprising an actuation mechanism for moving at least one of the first and second opposing jaw members towards and away from the other.

5. The apparatus of claim 4 wherein the means for elongating comprise a resiliently deformable portion of the first jaw member, the resiliently deformable portion having a central projecting portion that flattens as the first jaw member closes towards the second jaw member.

6. The apparatus of claim 4 further comprising an axially oriented slot adapted to extend through the engagement plane and a blade disposed for reciprocation along the axially oriented slot.

7. The apparatus of claim 4 further comprising a channeling electrode disposed at least partially intermediate the first and second bi-polar electrodes.

8. The apparatus of claim 1 further comprising a sensor disposed on one of the first and second members.

9. The apparatus of claim 8 further comprising an RF power controller that modulates the RF energy responsive to an output of the sensor.

10. A method for welding a vessel comprising:

identifying a vessel to be sealed, the vessel having first and second ends;

grasping the vessel at the first and second ends;

contacting a resiliently deformable element against an intermediate portion of the vessel at a location between the first and second ends;

flattening the resiliently deformable element to progressively engage the intermediate portion of the vessel located between the first and second ends to squeeze fluid out;

contacting first and second bi-polar electrodes to the vessel in spaced apart relation; and applying an RF current between the first and second electrodes so that the RF current flows through and welds the intermediate portion of the vessel.

11. The method of claim 10 further comprising, prior to contacting the first and second bi-polar electrodes to the vessel in spaced apart relation, collapsing the intermediate portion of the vessel to approximate opposing vessel walls.

12. The method of claim 10 wherein progressively engaging the intermediate portion of the vessel further comprises altering an impedance of the intermediate portion.

13. The method of claim 12 wherein progressively engaging the intermediate portion of the vessel further comprises reducing an extracellular fluid content of the vessel.

14. The method of claim 12 wherein progressively engaging the intermediate portion of the vessel to alter an impedance of the intermediate portion further comprises making the impedance of the intermediate portion substantially uniform.

15. The method of claim 10 further comprising contacting a channeling electrode to the intermediate portion of the vessel so that the RF current flowing between the first and second electrodes flows through and welds the intermediate portion of the vessel in contact with the channeling electrode.

16. The method of claim 10 further comprising contacting a sensor to the intermediate portion of the vessel.

17. The method of claim 16 wherein the sensor monitors temperature of the intermediate portion of the vessel and generates an output signal, the method further comprising modulating the RF current applied to the intermediate portion responsive to the output signal.

18. The method of claim 17 wherein the sensor monitors impedance of the intermediate portion of the vessel and generates an output signal, the method further comprising modulating the RF current applied to the intermediate portion responsive to the output signal.

19. The method of claim 10 further comprising:

monitoring energy delivered to the intermediate portion of the vessel;

generating an output signal corresponding to the energy delivered to the intermediate portion of the vessel; and modulating the RF current applied to the intermediate portion responsive to the output signal.

* * * * *